(12) United States Patent
Henry

(10) Patent No.: US 10,278,998 B2
(45) Date of Patent: May 7, 2019

(54) AGONIST MIXTURE FOR FAST MUCOKINETIC PATHWAY

(71) Applicant: Judy Colleen Henry, Coeur d'Alene, ID (US)

(72) Inventor: Judy Colleen Henry, Coeur d'Alene, ID (US)

( * ) Notice: Subject to any disclaimer, the term of this patent is extended or adjusted under 35 U.S.C. 154(b) by 0 days.

(21) Appl. No.: 15/709,449

(22) Filed: Sep. 19, 2017

(65) Prior Publication Data

US 2019/0083557 A1    Mar. 21, 2019

(51) Int. Cl.
| | | |
|---|---|---|
| A61K 36/00 | (2006.01) |
| A61K 36/074 | (2006.01) |
| A23L 33/105 | (2016.01) |
| A61K 9/00 | (2006.01) |
| A61K 45/06 | (2006.01) |
| A61M 15/00 | (2006.01) |

(52) U.S. Cl.
CPC .......... *A61K 36/074* (2013.01); *A23L 33/105* (2016.08); *A61K 9/0073* (2013.01); *A61K 45/06* (2013.01); *A61M 15/00* (2013.01)

(58) Field of Classification Search
CPC ...................................................... A61K 36/00
See application file for complete search history.

(56) References Cited

U.S. PATENT DOCUMENTS

2004/0109906 A1* 6/2004 Gafner ................. A61K 36/539
424/741

FOREIGN PATENT DOCUMENTS

CN        105943501 A  *  9/2016

* cited by examiner

*Primary Examiner* — Qiuwen Mi
(74) *Attorney, Agent, or Firm* — Timberline Patent Law Group PLLC; Mark Farrell

(57) ABSTRACT

An agonist mixture for activating a fast mucokinetic pathway is provided. An example method includes selecting agents for activating the complete mucokinetic pathway, determining proportions of the selected agents for activating the complete mucokinetic pathway in a mixture containing the selected agents, and administering the mixture to a user from a vaporizer, an inhaler, a mister, an e-cigarette, a sprayer, an atomizer, or a pressurized can. The method may further include administering to the user a mixture to be inhaled for nicotine withdrawal.

1 Claim, 3 Drawing Sheets

US 10,278,998 B2

AGONIST MIXTURE FOR FAST MUCOKINETIC PATHWAY

BACKGROUND

Maintenance of healthy lungs is important, especially for those exposed to air pollution. Clearance of foreign particles from the lungs is an important bodily defense. The clearance process is ongoing for maintaining ventilation and respiration in the lungs during normal health, or returning the lungs to health during times of sickness. The bodily processes that clear inhaled foreign matter from the airway passages often use mucus as part of the clearance mechanism. The body responds to inflammation and infections by creating more mucosal secretions. Mucus forms a good bodily defense since it traps foreign particles and is moved out of the body by movement of cilia, and other kinetic mechanisms. At a certain point, contaminated mucus, or sputum, is often cleared by coughing. Expectorants and mucolytic agents are example medications intended to promote the clearance of mucus from the lungs. There are various ingestible and inhalable agents that can each individually improve a single parameter of lung health. But none of the individual agents can initiate and maintain an entire mucokinetic pathway, from start to finish.

SUMMARY

An agonist mixture for activating a fast mucokinetic pathway is provided. An example method includes selecting agents for activating the complete mucokinetic pathway, determining proportions of the selected agents for activating the complete mucokinetic pathway in a mixture containing the selected agents, and administering the mixture to a user from a vaporizer, an inhaler, a mister, an e-cigarette, a sprayer, an atomizer, or a pressurized can. The method may further include administering to the user a mixture to be inhaled for nicotine withdrawal.

This summary is not intended to identify key or essential features of the claimed subject matter, nor is it intended to be used as an aid in limiting the scope of the claimed subject matter.

DETAILED DESCRIPTION

Overview

Figure 1:
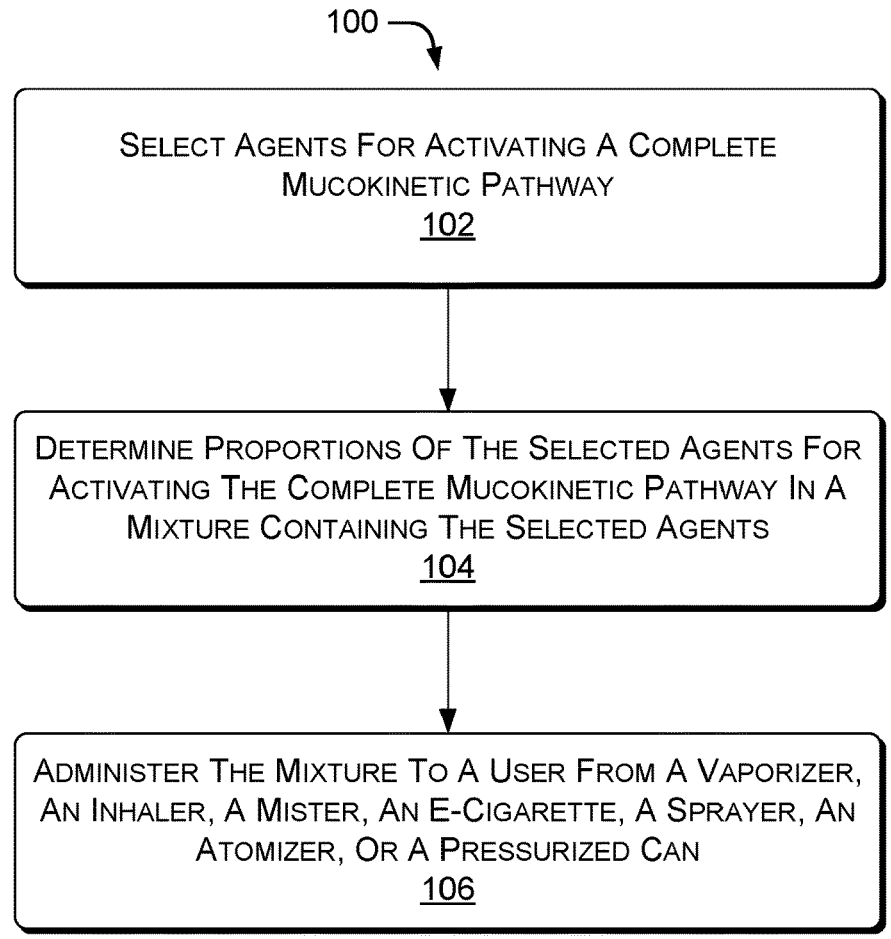
FIG. 1 is a flow diagram of an example general method of activating a mucokinetic pathway using a mixture of agents.

This disclosure describes example agonist mixtures for cascading a mucokinetic pathway. The example mixtures described herein are intended to have a beneficial effect on the human body in general, and to aid in the treatment of specific conditions. In an implementation, an example mixture initiates and synergizes a sequential cascade of respiratory responses in order to activate and maintain for a time a desirable mucokinetic pathway. The example mixture may be used for healthy lung maintenance, as a conditioner, or in an embodiment as an expectorant during times of sickness or stress to the lungs. The example mixture may also be used as an aid for easing asthma, bronchitis, and potentially for cystic fibrosis. In another implementation, an example mixture may stimulate strength of immune responses, for use during sickness or withdrawal from addictive agents.

Example Agonist Mixture for Activating a Mucokinetic Pathway

Although there are individual agents directed to modifying single airway parameters in humans, the example mixtures described herein have formulations that aim to establish and accelerate a sequence of events in a mucokinetic pathway: an ordered sequence of responses that have enhanced efficacy for lung health. The mucokinetic pathway is a set of systemic, nervous, pulmonary, cardio, and sometimes pleural responses that aid the human body in maintaining lung and airway health and in clearing the lungs when congested to achieve a toned and conditioned state of the lungs.

In an implementation, the example mixture contains one or more agents for reducing inflammation, since inflammation often accompanies maladies that cause sputum production. Asthma, chronic bronchitis, and cystic fibrosis, for example, each go hand-in-hand with chronic inflammation. Airways narrowed as a result of the inflammatory response cause wheezing.

Next, the example mixture aims to change a local water balance, by stimulating the body to draw local fluids, and secrete water into airways, a response that the body uses to make mucus more watery, as watery mucus is more easily cleared.

The example mixture may include a thinning agent, as secretion clearance can depend upon mucus properties such as viscosity, elasticity, and adhesiveness, as well as ciliary function. The transport of mucus by ciliary clearance can be impeded when the mucus has high viscosity, yet higher viscosity can also make the cough mechanism more effective in some circumstances.

Surface properties of both the airway linings and the mucus itself can play a significant role in secretion transport. In an implementation, the example mixture may contain a surfactant to modify the stickiness or adhesiveness of a secretion, or to modify surface tension between secretions and the airway linings.

Ciliary function can play a large role in transporting foreign particles and pollutants out of the lungs. Ciliary action can be dependent on temperature, hydration, and ciliary beat power, frequency, and wavelike coordination. Ciliary clearance can be detrimentally affected when the mucous is more viscous and adhesive. Ciliary action can also be negated by irritants, as described below, even though the ciliary function seeks to rid the body of the irritants.

Both sympathetic and parasympathetic nerves innervate the smooth muscles of the lung's airways. These nerves can either constrict or dilate an airway. The example mixture may contain an agent to constrict or an agent to dilate airways depending on intended use. Generally dilation is better for increasing airflow to improve mucous transport, but sometimes constriction can enable better transport of a built-up bolus in certain sizes of bronchioles.

Bronchial spasms (or bronchospasms) are a sudden constriction of the muscles in the walls of the bronchioles. These spasms can be caused by release of substances from immune system cells. These spasms can cause mild to severe breathing difficulties. Inflamed airways and bronchoconstriction are common in asthma. Bronchospasms appear as a feature in asthma, chronic bronchitis, and anaphylactic reactions. The example mixture may contain an agent to suppress or decrease bronchospasms.

The cough reflex may be useful for gross transport, but is not always desirable to induce when maintaining good health in healthy lungs, for example. In an implementation, the example mixture may be formulated to maintain a normal state of non-coughing or even suppress coughing, when the lungs are already healthy, in order to maintain health and enhance preventive transport of foreign impurities from lungs, for example.

Irritants obviously affect lung health. Exposure to irritants from pollution or smoking may result in inflammation, bronchitis, COPD, emphysema, or lung cancer, for example. Acute exposure to many types of irritants usually causes increased secretion of watery mucous that is relatively easily transported out of the lungs. In an implementation, an example mixture provides a defense against irritants, and one example mixture can help withdrawal from nicotine, for example.

Example Mixture

In an implementation, an example mixture contains agents to initiate a sequence of bodily reactions that constitute a mucokinetic pathway. The mixture thereby eases respiratory distress, including one or more agents to modulate inflammation, one or more agents to stimulate water secretions and thin mucus, one or more agents for reducing bronchospasms, one or more agents for soothing tissues, and one or more agents to stimulate expectoration of mucus, for example.

FIG. 1 shows an example general method 100 of activating a mucokinetic pathway using a mixture of agents. In the flow diagram of FIG. 1, operations of the example method 100 are shown in individual blocks.

At block 102, agents are selected for activating a complete mucokinetic pathway.

At block 104, proportions of the selected agents are determined for activating the complete mucokinetic pathway in a mixture containing the selected agents.

At block 106, the mixture is administered to a user from a vaporizer, an inhaler, a mister, an e-cigarette, a sprayer, an atomizer, or a pressurized can.

In an implementation, a compact and fast-acting mixture has agents that activate the segments of an example mucokinetic pathway. Each agent may serve more than one purpose, resulting in a compact mixture. In an implementation, the example mixture has the following formulation:

*Ganoderma lucidum* (e.g., Reishi mushroom) 41-47% by weight
*Pueraria lobata* (e.g., Kudzu root) 10-12% by weight
*Verbascum thapsus* (e.g., Mullein leaf) 20-24% by weight
*Inula helenium* (e.g., Elcampane root) 10-12% by weight
*Grindelia squarrosa* or *camporum* (e.g., *Grindelia* leaf & stem) 10-12% by weight In an implementation, the example mixture is made fast-acting by making the mixture into an aerosol or colloid, or vaporizing extracts of the agents or vaporizing the agents themselves to be used as an inhalant. The mixture, which does not exclude other carriers or diluents, may then be administered from a vaporizer, an inhaler, a mister, an e-cigarette, a sprayer, an atomizer, or an aerosol maker, for example.

Figure 2:
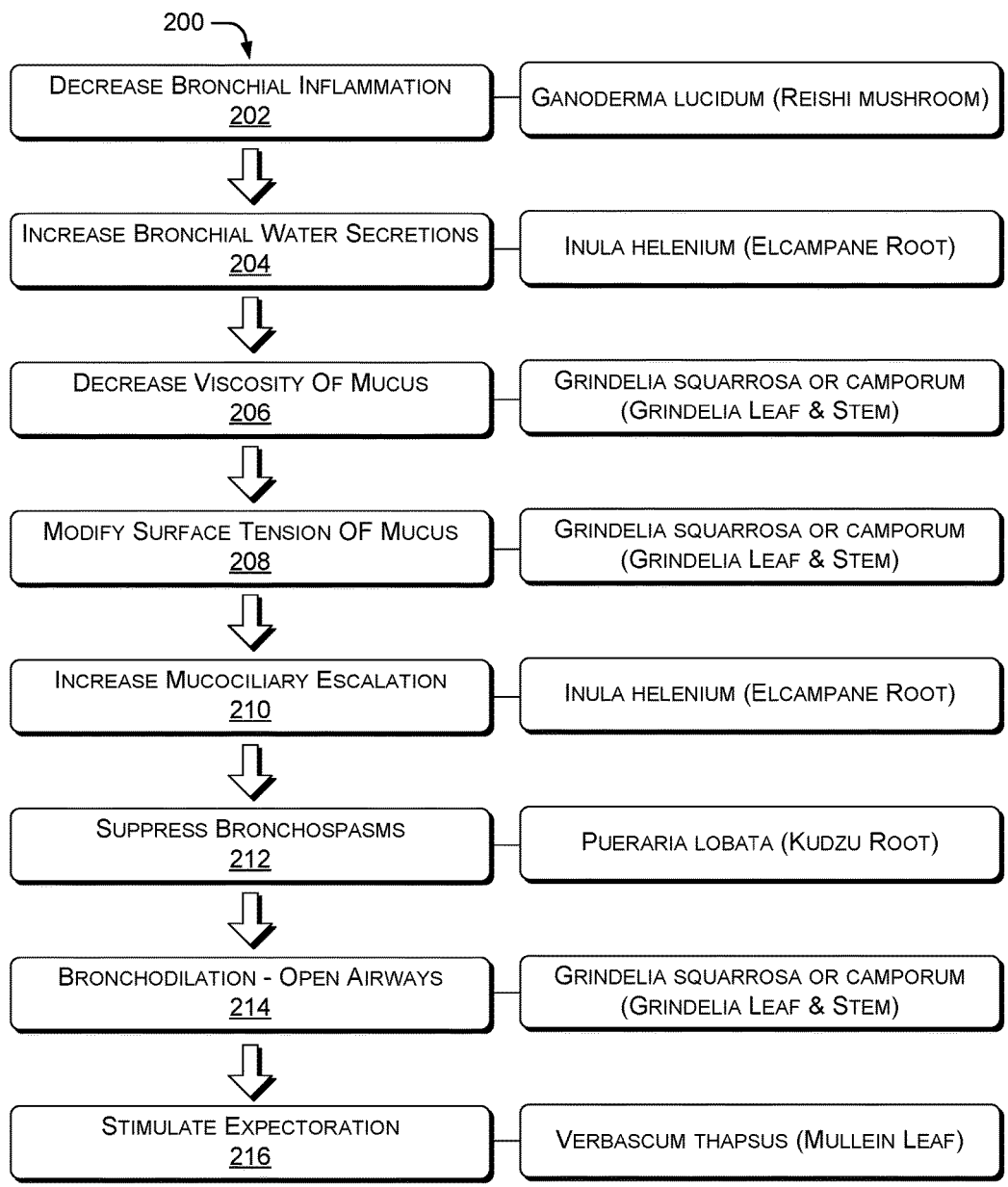
FIG. 2 is a flow diagram of an example method of activating a fast mucokinetic pathway using a compact mixture of agents.

FIG. 2 shows an example method 200 of activating a fast mucokinetic pathway using a compact mixture of agents. In the flow diagram of FIG. 2, operations of the example method 200 are shown in individual blocks.

At block 202, bronchial inflammation is suppressed by *Ganoderma lucidum* administered as a 41-47% by weight component of the total active ingredients of an inhalant.

At block 204, bronchial water secretions are increased by *Inula helenium* administered as a 10-12% by weight component of the total active ingredients of the inhalant.

At block 206, the viscosity of mucus is decreased by *Grindelia squarrosa* or *Grindelia camporum* administered as a 10-12% by weight component of the total active ingredients of the inhalant.

At block 208, the surface tension of the mucus is modified by the *Grindelia squarrosa* or *Grindelia camporum* administered as the 10-12% by weight component of the total active ingredients of the inhalant.

At block 210, mucociliary escalation is increased by the *Inula helenium* administered as a 10-12% by weight component of the total active ingredients of the inhalant.

At block 212, bronchospasms are suppressed by *Pueraria lobata* administered as a 10-12% by weight component of the total active ingredients of the inhalant.

At block 214, bronchodilation is activated by the *Grindelia squarrosa* or the *Grindelia camporum* administered as the 20-22% by weight component of the total active ingredients of the inhalant.

At block 216, expectoration is stimulated by *Verbascum thapsus* administered as a 20-24% by weight component of the total active ingredients of the inhalant.

The relative proportions as described above are important for activating an entire mucokinetic pathway. Out-of-range quantities of the same agents will not provide the same effect.

Quantities of the active agents included above are described in terms of weight percentages of the total weight of active ingredients in a mist, spray, vapor, vaporized mixture, aerosol, or inhalant, which may also contain non-active ingredients. The non-active ingredients are considered diluents or carriers, and so do not affect the relative proportions of the active ingredients above when the example mixture is provided as a vapor or mist, for example. Thus, to get a stronger effect, more of the example mixture can be administered and inhaled, but the active agents still maintain their relative proportions within the greater amount of the example mixture administered.

Another example mixture restores lung health by aiding the user to withdraw from smoking, and specifically from addictive dependence on nicotine. Withdrawal effects include headache, nausea, anxiety, fatigue, and irritability, as well as the deleterious effects of smoke and combustion products in the lungs. The various herbal agents in an example mixture provide many beneficial effects such as relaxation, increased energy, soothing the stomach, helping with anxiety, etc., that may help the user withdraw from nicotine.

An example mixture is a smoking cessation product that provides the user with physiological support and can provide a calming, pleasurable feeling, for example, while the user withdraws from nicotine. Herbal extracts in the example mixture are selected to coordinate a set of desirable physical and mental effects without nicotine. The example mixture can be liquified or extracted, and then vaporized to liberate the volatile compounds contained within, or otherwise made into a mist, spray, aerosol, or inhalant.

Figure 3:
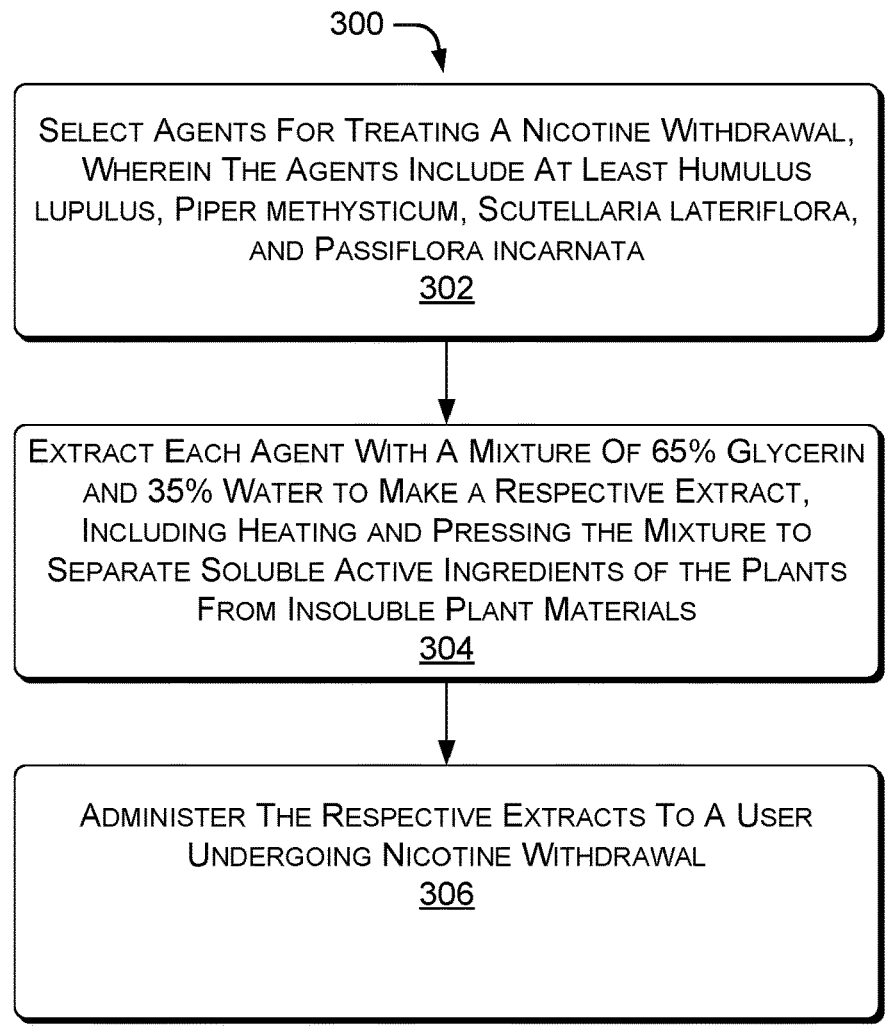
FIG. 3 is a flow diagram of an example method of supporting smoking cessation.

In an implementation, an example mixture contains:

*Humulus lupulus* (e.g., hops) 23-27% by weight
*Piper methysticum* (e.g., kava) 23-27% by weight
*Scutellaria lateriflora* (e.g., skullcap) 23-27% by weight
*Passiflora incarnata* (e.g., passionflower) 23-27% by weight FIG. 3 shows an example method of supporting smoking cessation. In the flow diagram of FIG. 3, operations of the example method 300 are shown in individual blocks.

At block 302, plants are selected to treat a nicotine withdrawal, wherein the plants include at least *Humulus lupulus, Piper methysticum, Scutellaria lateriflora*, and *Passiflora incarnata*.

At block 304, each plant is extracted with a mixture of 65% glycerin and 35% water to make a respective extract, including heating and pressing the mixture to separate soluble active ingredients of the plants from insoluble plant materials.

At block 306, the respective extracts are administered to a user undergoing nicotine withdrawal.

In an implementation, the example mixture may also include citric acid and/or black pepper extract. The combination of agents in this example mixture is selected to ease nicotine withdrawal symptoms and balance mood. The herbs can reduce anxiety to help cessation of smoking. This example mixture may be used alone, or in conjunction with the example mixture for activating a fast mucokinetic pathway.

The example mixtures may include other herbs, such as an herb from the group: abscess root, acai, aloe vera, alfalfa, arnica, asafoetida, ashoka tree, asthma plant, angelica, artichoke, astragalus, barberry, belladonna, bilberry, bitter gourd, basil, bitter leaf, bitter orange, burdock, black cohosh, boneset, brahmi, blessed thistle, blueberry, cayenne, California poppy, cat's claw, catnip leaf, chamomile, chaparral, calendula, catuaba, chaga, cilantro, chasteberry, cinchona, digitalis, damiana, dandelion root, devil's claw, devils club, elecampane, eleuthero root, elderberry, eucalyptus, echinacea, fenugreek, feverfew, flaxseed, garlic, ginger, ginkgo, ginseng, goldenrod, goldenseal, horehound, horsetail, hydrangea, hyssop, hawthorn, henna, hops flower, juniper, kava root, lady's mantle, licorice, linden, lobelia, lavender, lemon, licorice root, lotus, marigold, maca, maitake, maqui berry, marshmallow, milk thistle, motherwort, myrrh, nettle, neem, noni, oats, osha root, opium poppy, oregano, peppermint, passionflower leaf, raspberry, red root, saw palmetto, rosemary, red clover, sage, skullcap herb, St. John's wort, tea, thyme, turmeric, valerian, usnea, white oak, wild cherry, willow, wormwood, yarrow, yerba mansa, and *yucca*.

In one example mixture for aiding nicotine withdrawal, one or more of herbs chosen from black tea, California poppy, catnip leaf, hops flower, kava root, passionflower leaf, and/or skullcap herb is extracted with a solvent (such as a mixture of water and glycerin) to separate soluble materials from insoluble plant matter, such as cellulose.

In one embodiment a black tea extract comprises at least one compound chosen from theanine, caffeine, theophylline, thearubigin, and theaflavin. Theanine may be used for treating nicotine craving and/or providing one or more of the following physical or psychological benefits, such as reducing mental and physical stress, improved cognition, regulating blood sugar, and lowering anxiety. The caffeine may also be used for treating nicotine craving and/or providing one or more physical or psychological benefits, including stimulating the central nervous system and metabolism, reducing physical fatigue, and/or treating drowsiness. The theophylline may also be used for treating nicotine craving, as an alertness aid, an anti-inflammatory, and/or for increasing blood pressure or increasing heart rate.

Example Techniques

"Herbal extract" refers to an extract of an herb or herbs, such as formed by treating a part of a raw material with a solvent, such as water, glycerin, etc., and collecting the solvent that is enriched with soluble plant materials. An extract may exist in solid or liquid form. Most extracts of herbs, however, are performed with ethyl alcohol. These alcohol extractions are commonly known as tinctures. Ethanol, however, can have adverse effects by denaturing some of the organic compounds.

In one embodiment the disclosed compositions include at least one extract of a plant chosen from California poppy, Kava root, catnip leaf, hops flower, passionflower leaf, and/or skullcap herb. Such an herbal extract may be made by extracting the compounds from the herb that can elicit the wanted body reaction from the herb. For example, a portion of one or more herbs can be placed in a mixture of 65% glycerin and 35% water, heated, and then pressed to separate the soluble material from the insoluble plant material. In one embodiment, the resulting liquid is then used for extracting the next addition of the herb. This process may be repeated one or more times, until enough of the given agent has been extracted.

In another embodiment, the herb is extracted with a mixture of 65% glycerin and 35% water, heated, and then pressed to separate the soluble material from the insoluble plant material. Thereafter the insoluble plant material is additionally extracted one or more times with a fresh mixture of 65% glycerin and 35% water, heated, and then pressed to separate the soluble material from the insoluble plant material, and thereafter one or more of the extraction fractions are combined.

In the foregoing description and in the accompanying drawings, specific terminology and drawing symbols have been set forth to provide a thorough understanding of the disclosed embodiments. In some instances, the terminology and symbols may imply specific details that are not required to practice those embodiments. For example, any of the specific dimensions, quantities, material types, fabrication steps and the like can be different from those described above in alternative embodiments. The terms "example," "embodiment," and "implementation" are used to express an example, not a preference or requirement. Also, the terms "may" and "can" are used interchangeably to denote optional (permissible) subject matter. The absence of either term should not be construed as meaning that a given feature or technique is required.

Various modifications and changes can be made to the embodiments presented herein without departing from the broader spirit and scope of the disclosure. For example, features or aspects of any of the embodiments can be applied in combination with any other of the embodiments or in place of counterpart features or aspects thereof. Accordingly, the specification and drawings are to be regarded in an illustrative rather than a restrictive sense.

The invention claimed is:
1. A method for promoting healthy lungs, comprising:
  selecting agents for activating a complete mucokinetic pathway;
  determining proportions of the selected agents for activating the complete mucokinetic pathway in a mixture containing the selected agents;
  administering the mixture to a user from a vaporizer, an inhaler, a mister, an e-cigarette, a sprayer, an atomizer, or a pressurized can; and
  administering to the user a mixture to be inhaled for nicotine withdrawal, the mixture comprising 23-27% by weight *Humulus lupulus,* 23-27% by weight *Piper*

*methysticum,* 23-27% by weight *Scutellaria lateriflora,* and 23-27% by weight *Passiflora incarnata.*

\* \* \* \* \*